United States Patent
Wilson et al.

(10) Patent No.: US 11,642,127 B2
(45) Date of Patent: May 9, 2023

(54) SYSTEMS AND METHODS FOR END EFFECTOR POSITION SET POINT CORRECTION

(71) Applicant: INTUITIVE SURGICAL OPERATIONS, INC., Sunnyvale, CA (US)

(72) Inventors: Andrew D. Wilson, Menlo Park, CA (US); Amir Chaghajerdi, San Jose, CA (US); David W. Weir, San Carlos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 372 days.

(21) Appl. No.: 16/760,895

(22) PCT Filed: Nov. 2, 2018

(86) PCT No.: PCT/US2018/058900
§ 371 (c)(1),
(2) Date: Apr. 30, 2020

(87) PCT Pub. No.: WO2019/090047
PCT Pub. Date: May 9, 2019

(65) Prior Publication Data
US 2021/0177412 A1    Jun. 17, 2021

Related U.S. Application Data

(60) Provisional application No. 62/580,751, filed on Nov. 2, 2017.

(51) Int. Cl.
*A61B 17/072* (2006.01)
*A61B 34/35* (2016.01)
*A61B 17/00* (2006.01)

(52) U.S. Cl.
CPC ........ *A61B 17/07207* (2013.01); *A61B 34/35* (2016.02); *A61B 2017/00017* (2013.01);
(Continued)

(58) Field of Classification Search
CPC .... A61B 17/07207; A61B 2017/07271; A61B 2017/00017; A61B 2017/00022;
(Continued)

(56) References Cited

U.S. PATENT DOCUMENTS

| 8,452,447 B2 | 5/2013 | Nixon | |
|---|---|---|---|
| 2005/0230453 A1* | 10/2005 | Viola | A61B 17/07207 227/176.1 |

(Continued)

FOREIGN PATENT DOCUMENTS

| CN | 101683284 A | 3/2010 |
|---|---|---|
| CN | 103717152 A | 4/2014 |

(Continued)

OTHER PUBLICATIONS

International Preliminary Report on Patentability for Application No. PCT/US2018/058900, dated May 14, 2020, 16 pages.

(Continued)

*Primary Examiner* — Stephen F. Gerrity
*Assistant Examiner* — Linda J Hodge
(74) *Attorney, Agent, or Firm* — Artegis Law Group, LLP

(57) ABSTRACT

End effector position set point correction includes an instrument having an end effector and a control unit. In some embodiments, the control unit actuates the end effector to a first position, determines an actuation level, determines an offset based on the actuation level, adjusts a position set point based on the offset, and actuates the end effector to the adjusted position set point. In some embodiments, the control unit actuates the end effector, determines an actuation level, and determines whether the actuation level is above a threshold. In response to determining that the actuation level is above the threshold, the control unit determines a position of the end effector, identifies a nominal position associated with the determined position, determines an offset based on the nominal position and the determined position, adjusts a position set point based on the offset, and actuates the end effector to the adjusted position set point.

20 Claims, 6 Drawing Sheets

(52) U.S. Cl.
CPC ............... *A61B 2017/00367* (2013.01); *A61B 2017/07271* (2013.01)

(58) Field of Classification Search
CPC .. A61B 2017/0003; A61B 2017/00039; A61B 2017/00115; A61B 2017/00119; A61B 2017/00367; A61B 2017/00398; A61B 2017/00411; A61B 2017/2927; A61B 2090/0811; A61B 34/00; A61B 34/30; A61B 34/32
USPC .......................................... 227/175.1–182.1
See application file for complete search history.

(56) References Cited

U.S. PATENT DOCUMENTS

| | | |
|---|---|---|
| 2008/0283570 A1 | 11/2008 | Boyden et al. |
| 2010/0076474 A1 | 3/2010 | Yates et al. |
| 2012/0298719 A1 | 11/2012 | Shelton, IV et al. |
| 2014/0263541 A1 | 9/2014 | Leimbach et al. |
| 2015/0209035 A1* | 7/2015 | Zemlok ............ A61B 17/07207 73/1.01 |
| 2016/0331462 A1* | 11/2016 | Ranucci ............. A61B 17/0469 |
| 2017/0175964 A1 | 6/2017 | Patton |
| 2019/0102930 A1* | 4/2019 | Leimbach ........ A61B 17/07207 |
| 2019/0125459 A1* | 5/2019 | Shelton, IV ........... A61B 90/30 |
| 2022/0079586 A1* | 3/2022 | Shelton, IV ......... A61B 17/115 |

FOREIGN PATENT DOCUMENTS

| | | |
|---|---|---|
| CN | 104042269 A | 9/2014 |
| WO | WO-2016187008 A1 | 11/2016 |
| WO | WO-2017127202 A1 | 7/2017 |

OTHER PUBLICATIONS

International Search Report and Written Opinion for Application No. PCT/US2018/058900, dated Apr. 15, 2019, 22 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP18874593.9 dated Dec. 11, 2020, 06 pages.

* cited by examiner

SYSTEMS AND METHODS FOR END EFFECTOR POSITION SET POINT CORRECTION

RELATED APPLICATIONS

This patent application is a U.S. National Stage patent application of International Patent Application No. PCT/US2018/058900, filed on Nov. 2, 2018, the benefit of which is claimed, and claims priority to and benefit of the filing date of U.S. Provisional Patent Application No. 62/580,751, filed Nov. 2, 2017, entitled "Systems and Methods for End Effector Set Point Correction," each of which is incorporated by reference herein in its entirety.

TECHNICAL FIELD

Inventive aspects are directed towards the control of end effectors in teleoperated and robotic systems and more specifically to systems and methods for end effector position set point correction.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, traditional manual surgical instruments are being replaced by computer-assisted medical devices.

Minimally invasive surgical techniques using computer-assisted medical devices generally attempt to perform surgical and/or other procedures while minimizing damage to healthy tissue. Some minimally invasive procedures may be performed remotely through the use of computer-assisted medical devices with surgical instruments. With many computer-assisted medical devices, a surgeon and/or other medical personnel may typically manipulate input devices using one or more controls on an operator console. As the surgeon and/or other medical personnel operate the various controls at the operator console, the commands are relayed from the operator console to a patient side device to which one or more end effectors and/or surgical instruments are mounted. In this way, the surgeon and/or other medical personnel are able to perform one or more procedures on a patient using the end effectors and/or surgical instruments. Depending upon the desired procedure and/or the surgical instruments in use, the desired procedure may be performed partially or wholly under control of the surgeon and/or medical personnel using teleoperation and/or under semi-autonomous control where the surgical instrument may perform a sequence of operations based on one or more activation actions by the surgeon and/or other medical personnel.

Minimally invasive surgical instruments, whether actuated manually, teleoperatively, and/or semi-autonomously may be used in a variety of operations and/or procedures and may have various configurations. Many such instruments include an end effector mounted at a distal end of a shaft that may be mounted to the distal end of an articulated arm. In many operational scenarios, the shaft may be configured to be inserted (e.g., laparoscopically, thorascopically, and/or the like) through an opening (e.g., a body wall incision, a natural orifice, and/or the like) to reach a remote surgical site.

End effectors of different design and/or configuration may be used to perform different tasks, procedures, and functions so as to be allow the surgeon and/or other medical personnel to perform any of a variety of surgical procedures. Examples include, but are not limited to, cauterizing, ablating, suturing, cutting, stapling, fusing, sealing, etc., and/or combinations thereof. Accordingly, end effectors can include a variety of components and/or combinations of components to perform these surgical procedures.

Consistent with the goals of a minimally invasive procedure, the size of the end effector is typically kept small. One approach to keeping the size of the end effector small is to accomplish actuation of the end effector through the use of one or more inputs at a proximal end of the surgical instrument, where the proximal end is typically located externally to the patient. Various transmission components such as gears, levers, pulleys, cables, rods, belts, bands, and/or the like, may then be used to transmit actions from the one or more inputs along the shaft of the surgical instrument and to actuate the end effector. In the case of a computer-assisted, teleoperational medical device with an appropriate surgical instrument, a transmission mechanism at the proximal end of the instrument interfaces directly, or indirectly through other transmission components, with one or more actuators such as various motors, solenoids, servos, active actuators, hydraulics, pneumatics, and/or the like provided on an articulated arm of the patient side device or a patient side cart. The actuator(s) receive control signals produced in response to user commands provided through a master controller, and provide input to the instrument involving force and/or torque at the proximal end of the transmission mechanism; the various transmission elements ultimately transmit to actuate the end effector at the distal end of the transmission mechanism.

Minimally-invasive surgery was revolutionized with the advent of computer-assisted surgical systems, such as the da Vinci Surgical System commercialized by Intuitive Surgical. One innovation of the da Vinci Surgical System is the control of end effectors, such as the end effectors of surgical instruments, with high accuracy and high precision. As finer and more accurate control of end effectors is desired, it becomes important for control systems to accurately actuate the end effectors despite variations between end effectors, variations in end effectors over time, and/or the like.

Accordingly, it would be advantageous to have control systems that are able to accurately actuate end effectors despite variations among end effectors and more specifically to have control systems that are able to apply corrections to position set points used to actuate the end effectors.

SUMMARY

The following summary introduces certain aspects of the inventive subject matter in order to provide a basic understanding. This summary is not an extensive overview of the inventive subject matter, and it is not intended to identify key or critical elements or to delineate the scope of the inventive subject matter. Although this summary contains information that is relevant to various aspects and embodiments of the inventive subject matter, its sole purpose is to present some aspects and embodiments in a general form as a prelude to the more detailed description below.

Consistent with some embodiments, a system for actuating an instrument includes an instrument having an end effector and a drive mechanism for actuating the end effector and a control unit. The control unit is configured to actuate the end effector to a first position using the drive mechanism, determine an actuation level, determine a position offset based on the determined actuation level, adjust a position set point based on the position offset, and actuate the end effector to the adjusted position set point using the drive mechanism.

Consistent with some embodiments, a method of actuating an end effector of an instrument using a control unit includes actuating the end effector to a first position using a drive mechanism, determining an actuation level, determining a position offset based on the determined actuation level, adjusting a position set point based on the position offset, and actuating the end effector to the adjusted position set point using the drive mechanism.

Consistent with some embodiments, a non-transitory computer-readable medium having stored thereon a plurality of machine-readable instructions which when executed by one or more processors associated with a computer-assisted device are adapted to cause the one or more processors to perform a method. The method includes actuating an end effector of an instrument of the computer-assisted device to a first position using a drive mechanism, determining an actuation level, determining a position offset based on the determined actuation level, adjusting a position set point based on the position offset, and actuating the end effector to the adjusted position set point using the drive mechanism.

Consistent with some embodiments, a system for actuating an instrument includes an instrument comprising an end effector and a drive mechanism for actuating the end effector and a control unit. The control unit is configured to actuate the end effector using the drive mechanism, determine an actuation level during the actuation, and determine whether the actuation level is above a threshold actuation. The control unit is further configured to, in response to determining that the actuation level is above the threshold actuation, determine a position of the end effector, identify a nominal position associated with the determined position of the end effector, determine a position offset based on the nominal position and the determined position of the end effector, adjust a position set point based on the position offset, and actuate the end effector to the adjusted position set point using the drive mechanism.

Consistent with some embodiments, a method of actuating an end effector of an instrument using a control unit includes actuating the end effector using a drive mechanism, determining an actuation level during the actuation, and determining whether the actuation level is above a threshold actuation. The method further includes, in response to determining that the actuation level is above the threshold actuation, determining a position of the end effector, identifying a nominal position associated with the determined position of the end effector, determining a position offset based on the nominal position and the determined position of the end effector, adjusting a position set point based on the position offset, and actuating the end effector to the adjusted position set point using the drive mechanism.

Consistent with some embodiments, a non-transitory computer-readable medium having stored thereon a plurality of machine-readable instructions which when executed by one or more processors associated with a computer-assisted device are adapted to cause the one or more processors to perform a method. The method includes actuating an end effector of an instrument of the computer-assisted device using a drive mechanism, determining an actuation level during the actuation, and determining whether the actuation level is above a threshold actuation. The method further includes, in response to determining that the actuation level is above the threshold actuation, determining a position of the end effector, identifying a nominal position associated with the determined position of the end effector, determining a position offset based on the nominal position and the determined position of the end effector, adjusting a position set point based on the position offset, and actuating the end effector to the adjusted position set point using the drive mechanism.

Consistent with some embodiments, a system for actuating an instrument includes an instrument comprising an end effector and a drive mechanism for actuating the end effector and a control unit. The control unit is configured to actuate the end effector using the drive mechanism through a firing sequence, determine an aggregate actuation expended during the firing sequence, determine an adjustment to a reference position for the actuator based on the aggregate actuation, and store the adjusted reference position for use during a future actuation.

Consistent with some embodiments, a method of actuating an end effector of an instrument using a control unit includes actuating the end effector using a drive mechanism through a firing sequence, determining an aggregate actuation expended during the firing sequence, determining an adjustment to a reference position for the actuator based on the aggregate actuation, and storing the adjusted reference position for use during a future actuation.

Consistent with some embodiments, a non-transitory computer-readable medium having stored thereon a plurality of machine-readable instructions which when executed by one or more processors associated with a computer-assisted device are adapted to cause the one or more processors to perform a method. The method includes actuating an end effector of an instrument of the computer-assisted device using a drive mechanism through a firing sequence, determining an aggregate actuation expended during the firing sequence, determining an adjustment to a reference position for the actuator based on the aggregate actuation, and storing the adjusted reference position for use during a future actuation.

Consistent with some embodiments, a system for actuating an instrument includes an instrument comprising an end effector and a drive mechanism for actuating the end effector and a control unit. The control unit is configured to load a reference position of the end effector, shift a first position set point of a firing sequence relative to the reference position, actuate the end effector using the drive mechanism toward the first position set point, determine an actuation level during the actuation to the first position set point, determine whether the actuation level is above a threshold actuation, actuate the end effector through the firing sequence, determine an aggregate actuation expended during the firing sequence, determine an adjustment to the reference position for the actuator based on the aggregate actuation, and store the adjusted reference position for use during a future actuation. The control unit is further configured to, in response to determining that the actuation level is above the threshold actuation, determine a position of the end effector, identify a nominal position associated with the determined position of the end effector, determine a position offset based on the nominal position and the determined position of the end effector, adjust the first position set point based on the position offset, and actuate the end effector to the adjusted first position set point using the drive mechanism.

Figure 1:
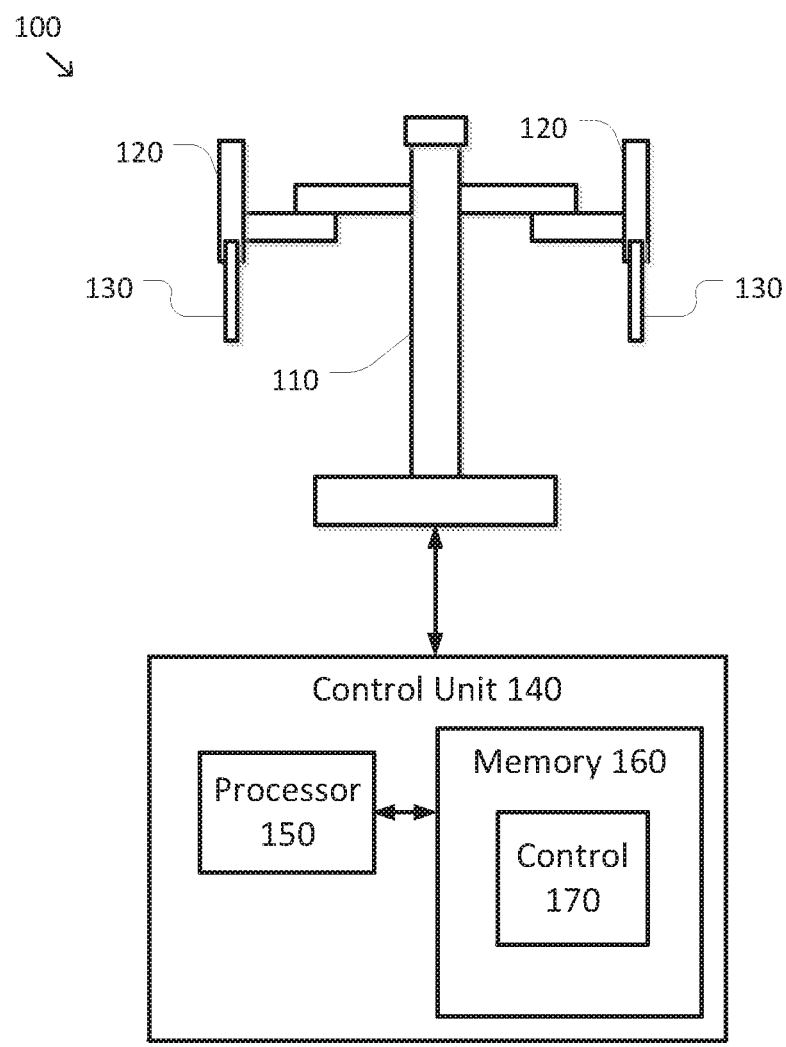
FIG. 1 is a simplified diagram of a computer-assisted system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the invention. For example, spatially relative terms-such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or application may, whenever practical, be included in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Aspects of the invention are described primarily in terms of an implementation using a da Vinci® Surgical System (specifically, a Model IS4000, marketed as the da Vinci® Xi™ Surgical System), commercialized by Intuitive Surgical, Inc. of Sunnyvale, Calif. Knowledgeable persons will understand, however, that inventive aspects disclosed herein may be embodied and implemented in various ways, including robotic and, if applicable, non-robotic embodiments and implementations. Implementations on da Vinci® Surgical Systems (e.g., the Model IS4000; the Model IS4200, commercialized as the da Vinci® X™ Surgical System) are merely exemplary and are not to be considered as limiting the scope of the inventive aspects disclosed herein. For example, any reference to surgical instruments and surgical methods is non-limiting as the instruments and methods described herein may be used for animals, human cadavers, animal cadavers, portions of human or animal anatomy, non-surgical diagnosis, industrial systems, and general robotic or teleoperational systems.

FIG. 1 is a simplified diagram of a computer-assisted system 100 according to some embodiments. As shown in FIG. 1, computer-assisted system 100 includes a computer-assisted device 110 with one or more movable or articulated arms 120. Each of the one or more articulated arms 120 may support one or more instruments 130. In some examples, computer-assisted device 110 may be consistent with a computer-assisted surgical device. The one or more articulated arms 120 may each provide support for medical instruments 130 such as surgical instruments, imaging devices, and/or the like. Examples of medical instruments 130 include surgical instruments for interacting with tissue, imaging or sensing devices, and/or the like. In some examples, the instruments 130 may include end effectors that are capable of, but are not limited to, performing, gripping, retracting, cauterizing, ablating, suturing, cutting, stapling, fusing, sealing, etc., and/or combinations thereof.

Computer-assisted device 110 is coupled to a control unit 140 via an interface. The interface may include one or more wireless links, cables, connectors, and/or buses and may further include one or more networks with one or more network switching and/or routing devices. Control unit 140 includes a processor 150 coupled to memory 160. Operation of control unit 140 is controlled by processor 150. And although control unit 140 is shown with only one processor 150, it is understood that processor 150 may be representative of one or more central processing units (CPUs), multi-core processors, microprocessors, microcontrollers, digital signal processors, graphics processing units (GPUs) field programmable gate arrays (FPGAs), application specific integrated circuits (ASICs), and/or the like in control unit 140. Control unit 140 may be implemented as a stand-alone subsystem and/or board added to a computing device or as a virtual machine. In some embodiments, control unit may be included as part of the operator workstation and/or operated separately from, but in coordination with the operator workstation.

Memory 160 may be used to store software executed by control unit 140 and/or one or more data structures used during operation of control unit 140. Memory 160 may include one or more types of machine readable media. Some common forms of machine readable media may include floppy disk, flexible disk, hard disk, magnetic tape, any other magnetic medium, CD-ROM, any other optical medium, RAM, PROM, EPROM, FLASH-EPROM, any other memory chip or cartridge, and/or any other medium from which a processor or computer is adapted to read.

As shown in FIG. 1, memory 160 includes a control application 170 that may be used to support autonomous, semiautonomous, and/or teleoperated control of computer-assisted device 110. Control application 170 may include one or more application programming interfaces (APIs) for receiving position, motion, force, torque, and/or other sensor information from computer-assisted device 110, articulated arms 120, and/or instruments 130 and their end effectors, exchanging position, motion, force, torque, and/or collision avoidance information with other control units regarding other devices, and/or planning and/or assisting in the planning of motion for computer-assisted device 110, articulated arms 120, and/or instruments 130. In some examples, control application 170 further supports autonomous, semiautonomous, and/or teleoperated control of the instruments 130 and their end effectors during a surgical procedure or other operation. And although control application 170 is depicted as a software application, control application 170 may optionally be implemented using hardware, software, and/or a combination of hardware and software.

In some embodiments, computer-assisted system 100 may be found in an operating room and/or an interventional suite. And although computer-assisted system 100 includes only one computer-assisted device 110 with two articulated arms 120, one of ordinary skill would understand that computer-assisted system 100 may include any number of devices with articulated arms and/or end effectors of similar and/or different design from computer-assisted device 110. In some examples, each of the devices may include fewer or more articulated arms and/or end effectors. In some examples, computer-assisted device 110 may be consistent with a da Vinci Surgical System.

Figure 2:
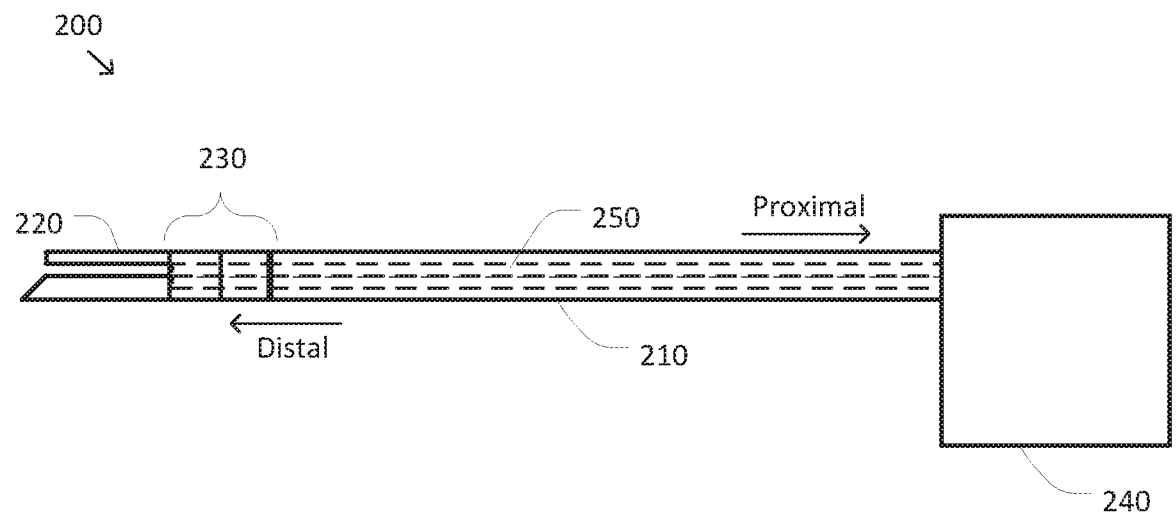
FIG. 2 is a simplified diagram showing an instrument according to some embodiments.

FIG. 2 is a simplified diagram showing an instrument 200 according to some embodiments. In some embodiments, instrument 200 may be consistent with any of the instruments 130 of FIG. 1. The directions "proximal" and "distal" as depicted in FIG. 2 and as used herein help describe the relative orientation and location of components of instrument 200. Distal generally refers to elements in a direction further along a kinematic chain from a user, a base of a computer-assisted device for holding the instrument 200, such as computer-assisted device 110, and/or or closest to a work site in the intended operational use of instrument 200. Proximal generally refers to elements in a direction closer along a kinematic chain toward the base of the computer-assisted device, a user or machine holding the instrument 200, and/or one of the articulated arms of the computer-assisted device for holding the instrument 200.

As shown in FIG. 2, instrument 200 includes a long shaft 210 coupling an end effector 220 located at a distal end of shaft 210 to where the instrument 200 is mounted to an articulated arm and/or a computer-assisted device at a proximal end of shaft 210. Depending upon the particular procedure for which the instrument 200 is being used, shaft 210 may be inserted through an opening in a patient or a work site (e.g., a body wall incision, a natural orifice, an access port, and/or the like) in order to place end effector 220 in proximity to a remote surgical or work site. As further shown in FIG. 2, end effector 220 is generally consistent with a two-jawed gripper-style end effector, which in some embodiments may further include a cutting and/or a stapling mechanism as is described in further detail below with respect to FIG. 3. However, one of ordinary skill would understand that different instruments 200 with different end effectors 220, such as end effectors with fasteners other than staples, are possible and may be consistent with the embodiments of instrument 200 as described elsewhere herein.

An instrument, such as instrument 200 with end effector 220 typically uses multiple degrees of freedom (DOFs) during its operation. Depending upon the configuration of instrument 200 and the articulated arm and/or computer-assisted device to which it is mounted, various DOFs that may be used to position, orient, and/or operate end effector 220 are possible. In some examples, shaft 210 may be inserted in a distal direction and/or retreated in a proximal direction to provide an insertion DOF that may be used to control how deep within the work site that end effector 220 is placed. In some examples, shaft 210 may be able rotate about its longitudinal axis to provide a roll DOF that may be used to rotate end effector 220. In some examples, additional flexibility in the position and/or orientation of end effector 220 may be provided by one or more joints and/or links, such as the joints and links of an articulated arm 120, located proximal to shaft 210 and instrument 200. In some examples, an optional articulated wrist 230 may be used to couple end effector 220 to the distal end of shaft 210. In some examples, articulated wrist 230 may optionally include one or more rotational joints, such as one or more roll, pitch or yaw joints that may provide one or more "roll," "pitch," and "yaw" DOF(s), respectively, that may be used to control an orientation of end effector 220 relative to the longitudinal axis of shaft 210. In some examples, the one or more rotational joints may include a pitch and a yaw joint; a roll, a pitch, and a yaw joint, a roll, a pitch, and a roll joint; and/or the like. In some examples, end effector 220 further includes a grip DOF used to control the opening and closing of the jaws of end effector 220 and/or an activation DOF used to control the extension, retraction, and/or operation of a stapling and cutting mechanism as is described in further detail below.

Instrument 200 further includes a drive system 240 located at the proximal end of shaft 210. Drive system 240 includes one or more components for introducing forces and/or torques to instrument 200 that can be used to manipulate the various DOFs supported by instrument 200. In some examples, drive system 240 may optionally include one or more motors, solenoids, servos, active actuators, hydraulics, pneumatics, and/or the like that are operated based on signals received from a control unit, such as control unit 140 of FIG. 1. In some examples, the signals may include one or more currents, voltages, pulse-width modulated wave forms, and/or the like. In some examples, drive system 240 may optionally include one or more shafts, gears, pulleys, rods, bands, and/or the like which may be coupled to corresponding motors, solenoids, servos, active actuators, hydraulics, pneumatics, and/or the like that are part of the articulated arm, such as any of the articulated arms 120, to which instrument 200 is mounted. In some examples, the one or more drive inputs, such as shafts, gears, pulleys, rods, bands, and/or the like, are used to receive forces and/or torques from the motors, solenoids, servos, active actuators, hydraulics, pneumatics, and/or the like and apply those forces and/or torques to adjust the various DOFs of instrument 200. In this discussion, both "force" and "torque" are sometimes used individually to indicate linear force, rotational torque, and/or both, as applicable.

In some embodiments, the forces and/or torques generated by and/or received by drive system 240 are transferred from drive system 240 and along shaft 210 to the various joints and/or elements of instrument 200 located distal to drive system 240 using one or more drive mechanisms 250. In some examples, the one or more drive mechanisms 250 may optionally include one or more gears, levers, pulleys, cables, rods, bands, and/or the like. In some examples, shaft 210 is hollow and the drive mechanisms 250 pass along the inside of shaft 210 from drive system 240 to the corresponding DOFs in end effector 220 and/or articulated wrist 230. In some examples, each of the drive mechanisms 250 may optionally be a cable disposed inside a hollow sheath or lumen in a Bowden cable like configuration. In some examples, the cable and/or the inside of the lumen may optionally be coated with a low-friction coating such as polytetrafluoroethylene (PTFE) and/or the like. In some examples, as the proximal end of each of the cables is pulled and/or pushed inside drive system 240, such as by wrapping and/or unwrapping the cable about a capstan or shaft, the distal end of the cable moves accordingly and applies a suitable force and/or torque to adjust one or more of the DOFs of end effector 220, articulated wrist 230, and/or instrument 200. Additional embodiments for drive system 240 and drive mechanisms are discussed in further detail below with respect to FIGS. 4 and 5.

Figure 3:
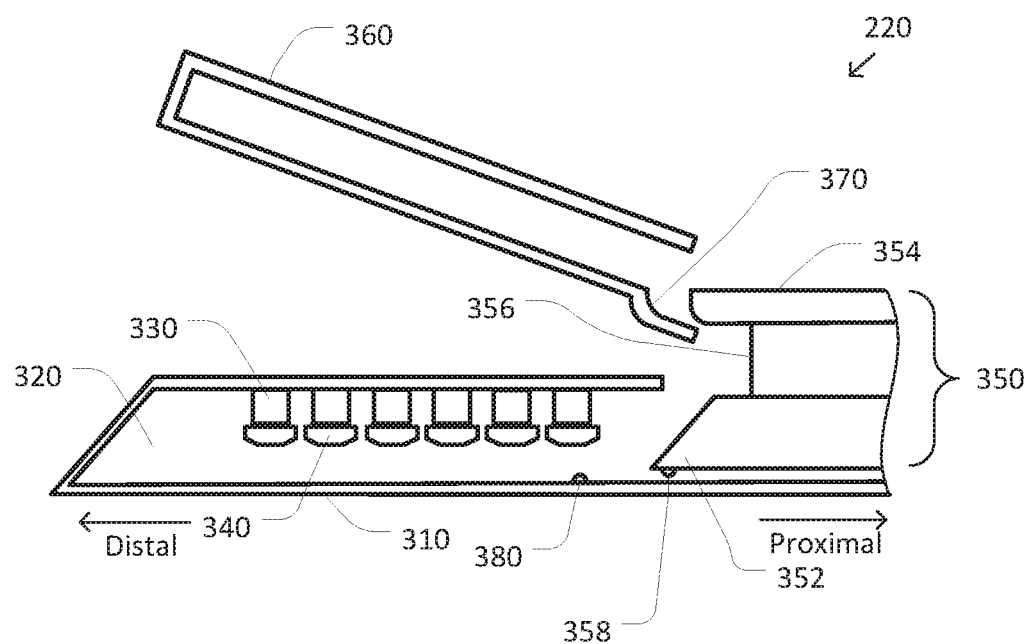
FIG. 3 is a simplified diagram of the end effector of FIG. 2 according to some embodiments.

FIG. 3 is a simplified diagram of end effector 220 according to some embodiments. As shown in FIG. 3, the distal end of instrument 200 or end effector 220 includes a mechanism for jaw closure and tissue stapling. And although end effector 220 is shown and described with one fixed and one movable jaw, one of ordinary skill would understand that the distal end of instrument 200 could be modified to use two movable jaws. It should be further understood that although the description below is in the context of a grasping and stapling instrument, the aspects so described may be applicable to instruments with or without cutting features, instruments supporting fusing rather than stapling, and/or the like.

FIG. 3 shows a cut-way side view of end effector 220 prior to actuation so that the jaws of end effector 220 are shown in an open position. As shown, end effector 220 includes a first jaw 310 that is generally fixed. Jaw 310 is designed to receive a replaceable staple cartridge 320 holding a plurality of staples 330 and a plurality of staple pushers 340. Staple cartridge 320 is designed to be replaceable so that end effector 220 is reusable by removing a first staple cartridge 320 after one or more of the staples 330 are used and replacing it with a second staple cartridge 320 having a new set of staples 330 that can be used to further perform a procedure. And although, staple cartridge 320 is shown with six staples 330 and six staple pushers 340 of uniform size, one of ordinary skill would understand that fewer or more staples, multiple rows of staples, staples of varying size and/or length are possible.

As further shown in FIG. 3, end effector 220 further includes a second jaw 360 that is movable about a pivot point (not shown) near its proximal end. In the context of a stapling instrument, second jaw 360 may alternatively be referred to as anvil 360. In the embodiments shown in FIG. 3, anvil 360 includes a transitional edge 370 configured so that upon initial actuation of end effector 220, a gap between anvil 360 and jaw 310 is rapidly reduced until material, such as tissue, is grasped between anvil 360 and jaw 310. Actuation of end effector 220 is accomplished by movement of a reciprocating element 350 from the proximal end of end effector 220 to the distal end of end effector 220. Reciprocating element 350 is coupled to the distal end of one or more of the drive mechanisms 250.

Reciprocating element 350 includes a sled 352 and a flange 354 with an optional cutting blade 356 coupled between the sled 352 and flange 354. As end effector 220 is actuated for stapling, sled 352 is propelled along within jaw 310 and staple cartridge 320 as reciprocating element 350 is pushed by drive mechanism 250. Sled 352 includes a wedge-shaped leading or distal end such that, as the leading end encounters each of the staple pushers 340, the leading end pushes the staple pushers 340 against corresponding staples 330. This action results in the firing of each of the staples 330 through the grasped material. Although sled 352 is shown with a single wedge at its leading edge, sled 352 may optionally include separate wedges for different rows of staples 330 and staple pushers 340 in staple cartridge 320. In some embodiments, staple pushers 340 are optional and the leading edge of sled 352 pushes directly against staples 330. As sled 352 is being propelled along within jaw 310 and staple cartridge 320, flange 354 is propelled along within anvil 360.

According to some embodiments end effector 220 is designed to be operated using staple cartridges 320 that accommodate staples 330 of different lengths. As can be inferred from FIG. 3, the distance that sled 352 travels before its leading edge encounters the first of staple pushers 340 (or staples 330 when stable pushers 340 are not used) varies based on staple length. For example, longer staples 330 are first encountered with less distal movement of sled 352 relative to shorter staples 330. Thus, the length of sled 352 travel before encountering the first staple pusher 340 (or staple 330) can be used to determine a length of staples 330 in staple cartridge 320. In some examples, the staple length may be determined by detecting a location of sled 352 and/or reciprocating element 350 when an increase in force or torque used to actuate reciprocating element 350 is detected. However, because the amount of force used to fire a staple 330 through a material may be highly variable (e.g., due to no material at a location of the first staple, material of varying thickness and/or toughness, and/or the like) a detent 358 located on sled 352 and a corresponding detente 380 in staple cartridge 320 are used to ensure that a minimum increase in actuation force or torque occurs when sled 352 encounters the first staple pusher 340 (or the first staple 330). In some embodiments, additional mechanisms (not shown) may also be included to detect the absence of staple cartridge 320 and/or the presence of a staple cartridge 320 whose staples 330 have already been fired. In some examples, the location of detent 380 may also be used to identify other features of staple cartridge 320, such as staple style, a number of rows of staples, and/or the line. In some examples, two or more detents could be used to signify a pattern of locations where increased actuation is expected to indicate staple length, staple style, number of rows of staples, and/or the like. The use of detents and other mechanisms to detect staple length and/or other staple cartridge conditions are described in more detail in co-owned International Patent Application No. PCT/US2017/50747, filed on Sep. 8, 2017 and disclosing "Stapler Reload Detection and Identification," the disclosure of which is incorporated by reference herein.

Additionally, as the leading distal end of flange 354 encounters transitional edge 370, flange 354 causes initial rapid closure of the gap between anvil 360 and jaw 310. Cutting blade 356 is located somewhat proximally to the distal ends of sled 352 and flange 354 so that cutting of any grasped material trails the firing of the staples 330.

Figure 4:
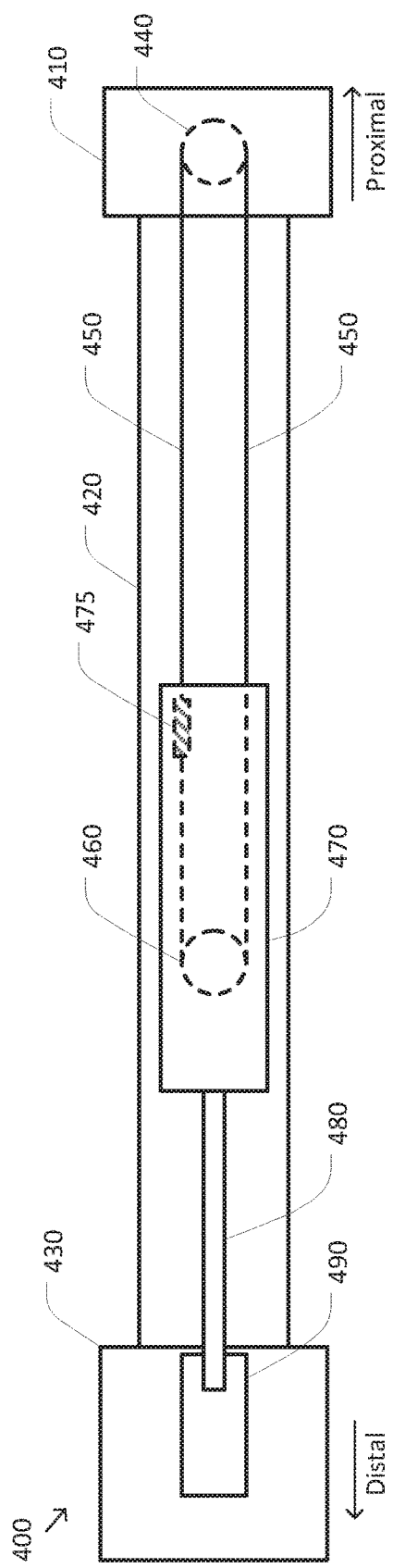
FIGS. 4 and 5 are simplified cross-sectional diagrams of drive mechanisms used to actuate an end effector according to some embodiments.

FIG. 4 is a simplified cross-sectional diagram of a drive mechanism 400 used to actuate an end effector according to some embodiments. As shown in FIG. 4, drive mechanism 400 includes a cable-driven mechanism for transferring push and/or pull actuation forces and/or torques to an end effector 430. A drive system 410 is located at a proximal end of drive mechanism 400 and is coupled via a hollow shaft 420 to end effector 430. In some examples, drive system 410 may be consistent with drive system 240, hollow shaft 420 may be consistent with shaft 210 and/or end effector 430 may be consistent with end effector 220. Drive system 410 includes one or more actuators, such as one or more motors, servos, and/or the like, that are configured to rotate a proximal pulley 440. Wound around proximal pulley 440 is a cable 450, which extends distally along hollow shaft 420 and is wound around a distal pulley 460 at its distal end. Cable 450 is formed as a loop around proximal pulley 440 and distal pulley 460 and is kept sufficiently taught so that cable 450 does not slip as it pulled in either one direction or the other around proximal pulley 440 and distal pulley 460 by drive system 410. In some examples, cable 450 may be a coil pipe, braided cable, wire, and/or the like.

A shuttle 470 is attached to cable 450 using attachment hardware 475, such as a crimp, clamp, bolt, and/or the like. As cable 450 is pulled around proximal pulley 440 and distal pulley 460, shuttle 470 moves proximally and/or distally along hollow shaft 420. Mounted to shuttle 470 is an actuation rod 480 which couples the motion of shuttle 470 at its proximal end to a moveable component 490 of end effector 430. In some examples, moveable component 490 may be consistent with reciprocating element 350. Thus, in response to rotation of proximal pulley 440 by an actuator in drive system 410, moveable component 490 is able to be moved both proximally and distally so as to actuate a DOF of end effector 430. For example, the DOF may correspond to jaw clamping, staple firing, and/or the like.

Figure 5:
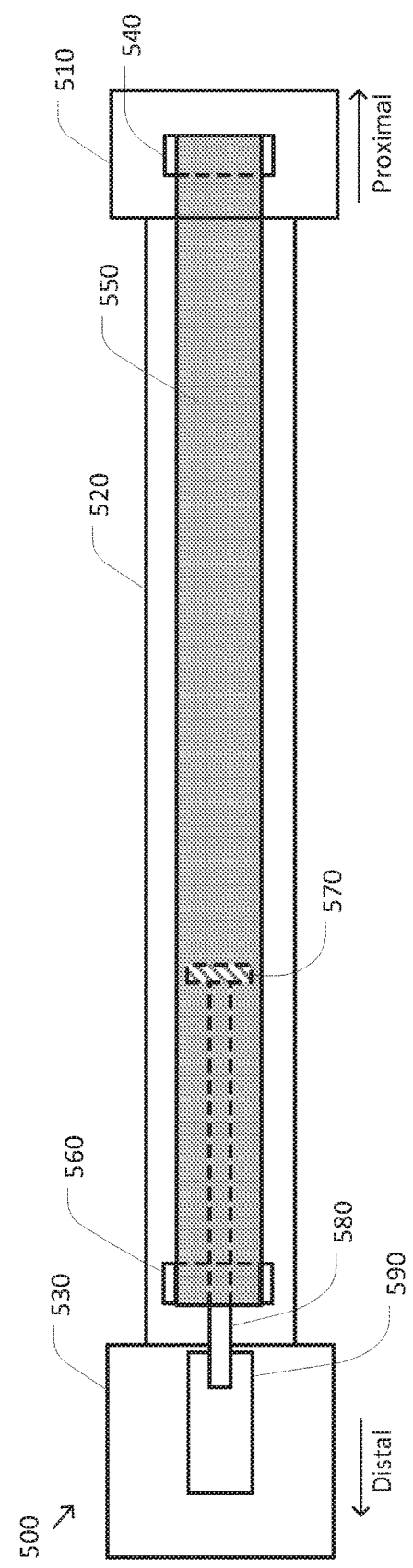

FIG. 5 is a simplified cross-sectional diagram of another drive mechanism 500 used to actuate an end effector according to some embodiments. As shown in FIG. 5, drive mechanism 500 includes a belt-driven mechanism for transferring push and/or pull actuation forces and/or torques to an end effector 530. A drive system 510 is located at a proximal end of drive mechanism 500 and is coupled via a hollow shaft 520 to end effector 530. In some examples, drive system 510 may be consistent with drive system 240, hollow shaft 520 may be consistent with shaft 210 and/or end effector 530 may be consistent with end effector 220. Drive system 510 includes one or more actuators, such as one or more motors, servos, and/or the like, that are configured to rotate a proximal pulley 540. Wound around proximal pulley 540 is a belt 550, which extends distally along hollow shaft 520 and is wound around a distal pulley 560 at its distal end. Belt 550 is formed as a loop around proximal pulley 540 and distal pulley 560 and is kept sufficiently taught so that belt 550 does not slip as it pulled in either one direction or the other around proximal pulley 540 and distal pulley 560 by drive system 510. In some examples, belt 550 may be a web, mesh, and/or the like.

An actuation rod 580 is attached to belt 550 using attachment hardware 570, such as a crimp, clamp, bolt, rivet, and/or the like. As belt 550 is pulled around proximal pulley 540 and distal pulley 560, actuation rod 580 moves proximally and/or distally along hollow shaft 520. A moveable component 590 of end effector 530 is mounted to a distal end of actuation rod 580. In some examples, moveable component 590 may be consistent with reciprocating element 350. Thus, in response to rotation of proximal pulley 540 by an actuator in drive system 510, moveable component 590 is able to be moved both proximally and distally so as to actuate a DOF of end effector 530. For example, the DOF may correspond to jaw clamping, staple firing, and/or the like.

Additional embodiments of drive mechanisms, such as drive mechanism 400 and 500 are described in more detail in co-owned International Patent Application No. PCT/US2017/50760, filed on Sep. 8, 2017 and disclosing "Push-Pull Surgical Instrument End Effector Actuation using Flexible Tension Member," the disclosure of which is incorporated by reference herein.

Under ideal operating and material conditions, an end effector, such as end effector 220, may be repeatedly actuated using a drive mechanism, such as drive mechanism 400 and/or 500, with complete accuracy in position between each actuation. However, in practice, the end effector and/or the drive mechanism are not ideal. Variations in manufacturing may result in differences in sizes and/or tolerances in the components of the end effector and/or the drive mechanism. In addition, the materials used to manufacture the end effector and/or the drive mechanism may not be ideally rigid and may be subject to stretching, compression, and/or slipping that may result in plastic and/or elastic deformation in the end effector and/or the drive mechanism. Further, repeated actuation may result in wear and tear that may affect a further actuation of the end effector. As a result, a known movement in an actuator of a drive system, such as drive system 240, 410, and/or 510, may not result in the same amount of motion in a DOF of the end effector over different actuations or in the same amount of motion in corresponding DOFs of different end effectors. This can result in incomplete firing of the end effector (e.g., a distal-most staple 330 may not fire completely, cutting blade 356 may not complete a cut, etc.), premature firing (e.g., firing or partial firing of a staple before a material is fully grasped), and/or the like. In some examples, these variations may be as large as 0.05 to 0.5 mm per actuation and up to 1.5 mm or more for an end effector having a DOF with a 100 mm long range. In some examples, these variations may be larger than the differences in the position of detent 380 between different staple cartridges 320 having staples of the same length or for staple cartridges having staples of different length, which may be as close together as 0.5 mm to 1.0 mm. In some examples, during operation, elastic deformation of the end effector may vary in the range of 0.1 mm to 6.0 mm when the end effector is actuated with a force as large as 1000 N. Thus, systems and methods for compensating and/or correcting for these variations are desirable so that high accuracy and high precision across multiple actuations using a given end effector and/or across different end effectors of a same type may be obtained.

Figure 6:
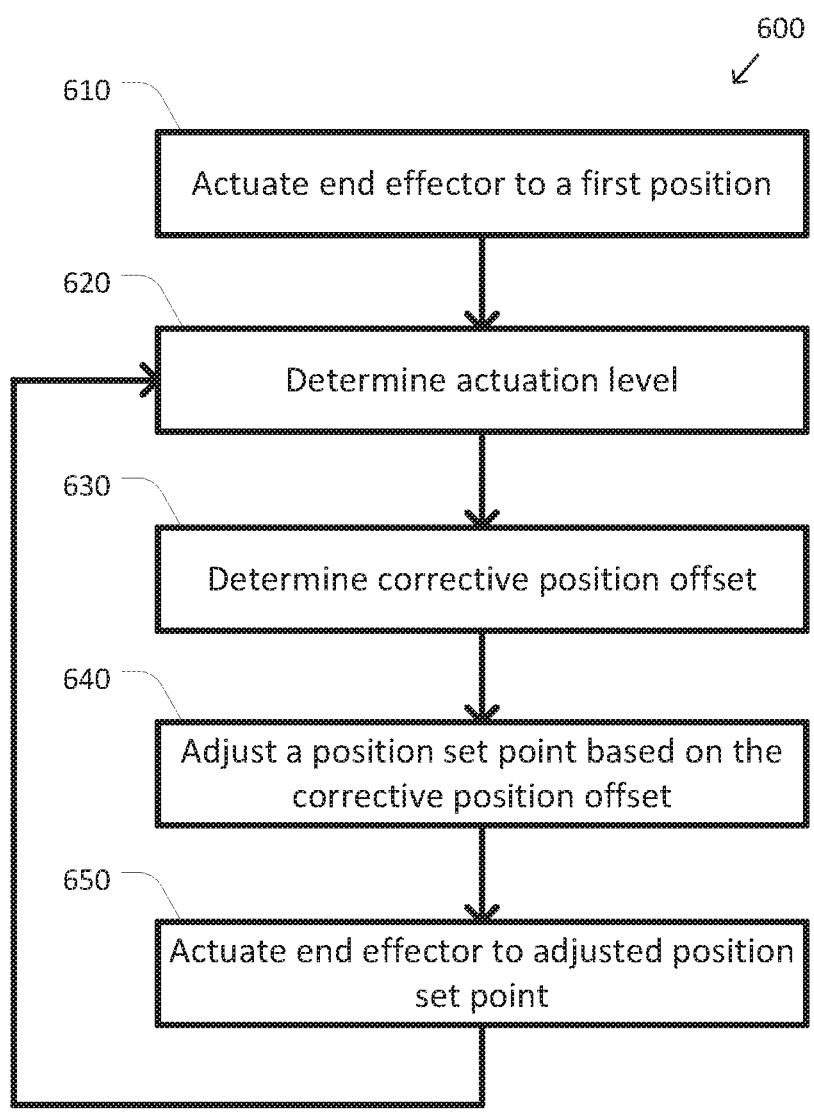
FIG. 6 is a simplified diagram of a method for correcting position set points of an end effector in response to elastic deformation in an instrument according to some embodiments.

FIG. 6 is a simplified diagram of a method 600 for correcting position set points of an end effector in response to elastic deformation in an instrument according to some embodiments. One or more of the processes 610-650 of method 600 may be implemented, at least in part, in the form of executable code stored on non-transitory, tangible, machine readable media. This executable code, when run by one or more processors (e.g., the processor 150 in control unit 140), may cause the one or more processors to perform one or more of the processes 610-650. In some embodiments, method 600 may be performed by an application, such as control application 170. In some embodiments, method 600 may be used to control the actuation of a reciprocating element, such as reciprocating element 350, by correcting one or more position set points in response to elastic deformation detected in a drive mechanism, such as drive mechanism 400 and/or 500. In some embodiments, the order of processes of method 600 may occur in a different order than those implied by the flow chart of FIG. 6. In some examples, processes 610 and 620 may be performed concurrently and/or processes 640 and/or 650 may be performed concurrently.

At a process 610, an end effector is actuated to a first position. In some examples, the end effector, such as end effector 220, may be actuated by sending one or more control signals to an actuator, such as actuator in drive system 240, 410, and/or 510. A drive mechanism, such as drive mechanism 250, 400, and/or 500, may then transfer the actuation of the actuator to a DOF in the end effector. In some examples, the DOF may correspond to the distal and/or proximal motion of a reciprocating element, such as reciprocating element 350. The first position may correspond to a known set point for a position control loop in a control unit for the DOF. In some examples, the first position may further correspond to movement of the reciprocating element to a first desired position. In some examples, the first position may correspond to a position indicated by the interaction of two detents, such as the detents 358 and 380. In some examples, arrival at the first position may be detected by tracking the kinematic chain of the end effector, tracking of one or more fiducial markers on the end effector, detecting an actuation level above and/or below a threshold, and/or the like. In some examples, the first position may correspond to a zero and/or other reference position of the end effector, the drive mechanism, the drive system, and/or the like.

At a process 620, an actuation level is determined. In order to actuate the end effector to the first position, the drive system and drive mechanism may have to apply varying levels of actuation that may depend on the specific end effector being actuated, the type and/or amount of material being manipulated by the end effector, and/or the like. For example, a more rigid material being grasped or a thick amount of material being grasped may require a higher actuation level in order to actuate the end effector to the first position. In some examples, the actuation level may be determined by measuring and/or computing an amount of current being drawn by the actuator in the drive system and detected using a current sensor, a force or torque being applied by the actuator and detected using a force or torque sensor, and/or other factors indicative of actuation level. In some examples, combination of two or more of current, force, torque, and/or the like may be used to determine the actuation level.

At a process 630, a corrective position offset is determined. In some examples, the actuation level determined during process 620 may be indicative of an amount of elastic deformation in the drive mechanism caused by slipping, flexing, stretching, and/or the like. For example, a higher actuation level due to more force or torque being applied by the actuator to move the DOF to the first position may result in a higher amount of slip, flex, and/or stretch, which results in the DOF not actually reaching the first position. In some examples, the actuation level may be proportional to the amount of slip, flex, and/or stretch and is a measure of an error (e.g., a shortfall) in reaching the first position. In some examples, the amount of positional error may be determined by modeling the drive mechanism using a spring model according to Equation 1, where F corresponds to the actuation level, k is a spring modeling constant, and x is the amount of position error.

$$F = k \cdot x \qquad \text{Equation 1}$$

In some examples, when the actuation level F corresponds to applied force, k may be in a range from 50,000 to 200,000 N/m. Using Equation 1 and the actuation level (F) determined during process 620, x is computed and corresponds to a corrective position offset, which is an amount of further actuation distance for the DOF to reach the actual first position. In some examples, the modeling constant k may be set based on type of end effector or instrument. In some examples, the modeling constant k may be determined empirically for each end effector and/or instrument and stored in a memory in the end effector or instrument and/or may be determined using a table and/or database accessible by the control unit based on an identifier for the end effector or the instrument.

At a process 640, a position set point is adjusted based on the corrective position offset determined during process 630. Further actuation of the end effector may include driving the end effector to the first position and/or to other positions (such as a full distal position in order to fire all the staples in a staple cartridge and/or to complete a cutting operation). Each of these positions may correspond to a position set point which may be corrected by adding the corrective positional offset to the position set point to obtain an adjusted position offset. For example, the set point used to "reach" the first position in process 610 may be adjusted by the corrective position offset to determine an adjusted position set point that corresponds to an actual amount the actuator has to actuate the drive mechanism to actually reach the first position.

At a process 650, the end effector is actuated to the adjusted position set point determined during process 640. In some examples, the actuation of process 650 may be similar to the actuation used during process 610. In some examples, the actuation to the adjusted set point may additionally be subject to a current, force, torque, and/or similar limit. In some examples, the adjusted position set point may be set as a new position set point for the position control loop. Once the end effector is actuated to the adjusted position set point, additional position set points may be adjusted by returning to process 620 to determine a new actuation level for adjusting another position set point.

As discussed above and further emphasized here, FIG. 6 is merely an example which should not unduly limit the scope of the claims. One of ordinary skill in the art would recognize many variations, alternatives, and modifications. In some embodiments, method 600 may use other approaches to apply correction to an actuation. In some examples, an additional process between processes 640 and 650 may actuate the end effector to the unadjusted position set point before then actuating the end effector to the adjusted position set point using process 650. In some examples, after completing process 650, method 600 may return to process 640 to adjust another position set point based on the previously determined corrective position offset. In some examples, after completing process 650, method 600 may return to process 610 where the end effector is actuated to a second position and then processes 620-650 are used to apply a correction to the actuation so that the end effector reaches the second position using the adjusted position set point for the second position. In this way, position set point adjustment occurs for each position set point in an actuation profile for the end effector. In some examples, processes 620-650 may be applied one or more times before the first position is reached so that the position set point for the first position may be adjusted before the end effector is fully actuated to the first position.

Figure 7:
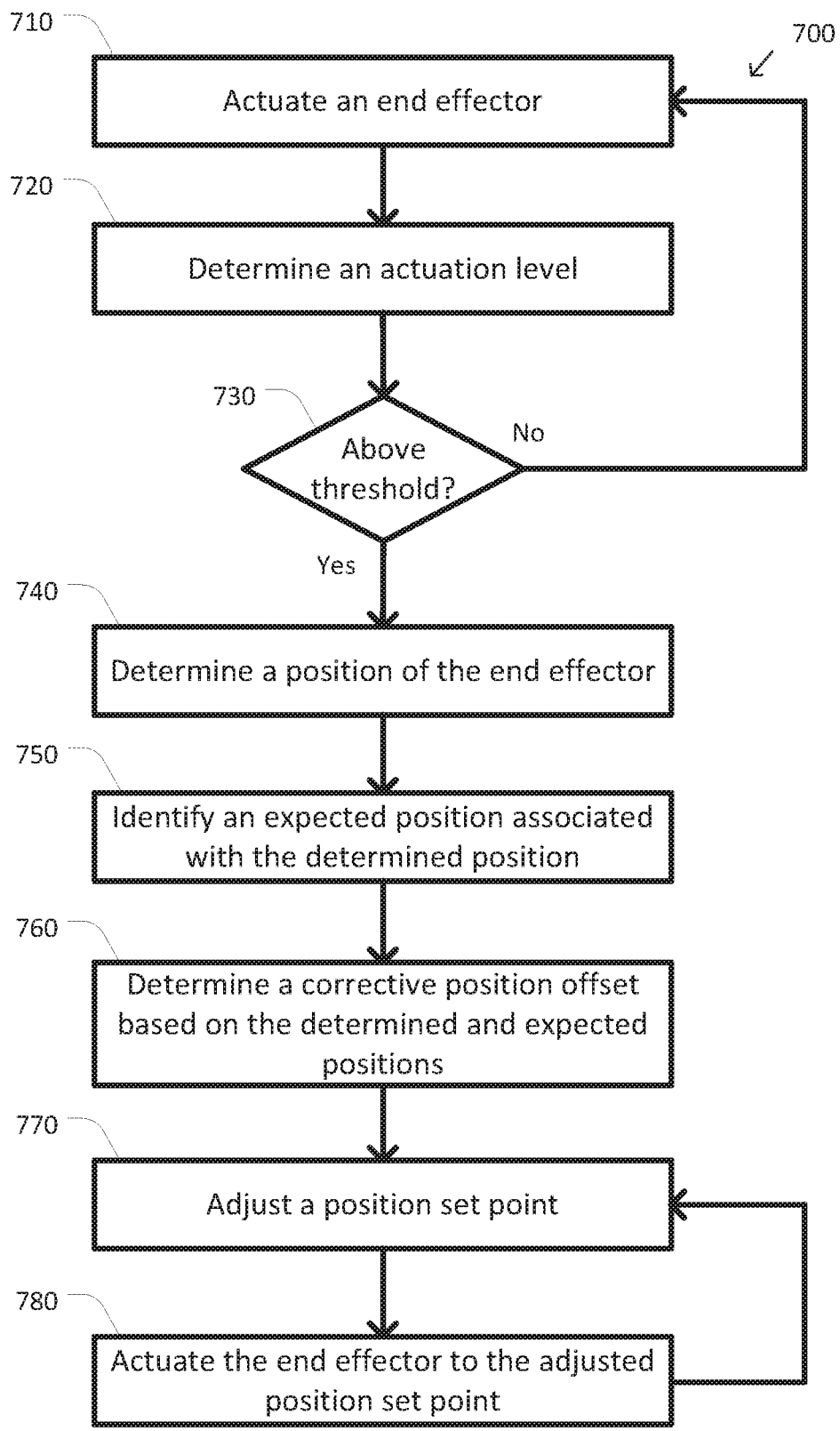
FIG. 7 is a simplified diagram of a method for correcting position set points of an end effector in response to variations in an instrument according to some embodiments.

FIG. 7 is a simplified diagram of a method for correcting position set points of an end effector in response to variations in an instrument according to some embodiments. One or more of the processes 710-780 of method 700 may be implemented, at least in part, in the form of executable code stored on non-transitory, tangible, machine readable media. This executable code, when run by one or more processors (e.g., the processor 150 in control unit 140), may cause the one or more processors to perform one or more of the processes 710-780. In some embodiments, method 700 may be performed by an application, such as control application 170. In some embodiments, method 700 may be used to control the actuation of a reciprocating element, such as reciprocating element 350, by correcting one or more position set points in response to variations detected during actuation of the end effector, such as due to elastic deformations, plastic deformations, end effector variations, and/or the like. In some embodiments, the order of processes of method 700 may occur in a different order than those implied by the flow chart of FIG. 7. In some examples, processes 710-730 may be performed concurrently and/or processes 770 and 780 may be performed concurrently.

At a process 710, an end effector is actuated. In some examples, the end effector, such as end effector 220, may be actuated by sending one or more control signals to an actuator, such as actuator in drive system 240, 410, and/or 510. A drive mechanism, such as drive mechanism 250, 400, and/or 500, may then transfer the actuation of the actuator to a DOF in the end effector. In some examples, the DOF may correspond to the distal and/or proximal motion of a reciprocating element, such as reciprocating element 350. In some examples, the end effector is actuated so as move the DOF in a first direction, such as distally in the example of reciprocating element 350.

At a process 720, an actuation level is determined. In order to actuate the end effector, the drive system and drive mechanism may have to apply varying levels of actuation that may depend on the specific end effector being actuated, the type and/or amount of material being manipulated by the end effector, and/or the like. For example, a more rigid material being grasped or a thick amount of material being grasped may require a higher actuation level in order to actuate the end effector to the first position. As the end effector is being actuated during process 710, the actuation level is periodically and/or constantly monitored. In some examples, the actuation level may be determined by measuring and/or computing an amount of current being drawn by the actuator in the drive system and detected using a current sensor, a force or torque being applied by the actuator and detected using a force or torque sensor, and/or other factors indicative of actuation level. In some examples, combination of two or more of current, force, torque, and/or the like may be used to determine the actuation level.

At a process 730, it is determined whether the actuation level determined during process 720 is above a threshold. In some examples, the threshold may correspond to an increase in actuation level associated with a detectable location within the range of the DOF of the end effector being actuated. In the examples of FIG. 3, the increase in action level above the threshold may correspond to detent 358 reaching detent 380 where an increase in actuation level occurs to move detent 358 past detent 380. In some examples, the threshold is configurable and may be set based on a type of end effector, a type of procedure, a type of material being manipulated, operator preference, and/or the like. In some examples, the threshold may be determined empirically for each end effector and/or instrument and stored in a memory in the end effector or instrument and/or may be determined using a table and/or database accessible by the control unit based on an identifier for the end effector or the instrument. When the action level has not gone above the threshold, further actuation of the end effector occurs by returning to process 710. When the actuation level goes above the threshold, a position offset for the end effector is determined beginning with process 740 before further actuation of the end effector occurs.

At the process 740, a position of the end effector is determined. In some examples, the position of the end effector may be determined by tracking the kinematic chain of the end effector, tracking of one or more fiducial markers on the end effector, tracking an amount of movement in the actuator, and/or the like. In some examples, the position of the end effector may be determined relative to a zero and/or other reference position of the end effector, the drive mechanism, the drive system, and/or the like.

At a process 750, an expected position of the end effector is determined. The position of the end effector determined during process 740 may not correspond to the expected position of the end effector, such as where a position of detent 380 is located for a staple cartridge 320 having staples of a specific length, a position of a mechanism to detect the absence of staple cartridge 320, and/or the position of a mechanism to detect the presence of a staple cartridge 320 whose staples 330 have already been fired. In some examples, the differences between the position of the end effector determined during process 740 and the expected position of the end effector may be due to elastic deformations, plastic deformations, bias in the deformations, end effector variations, and/or the like.

Figure 8:
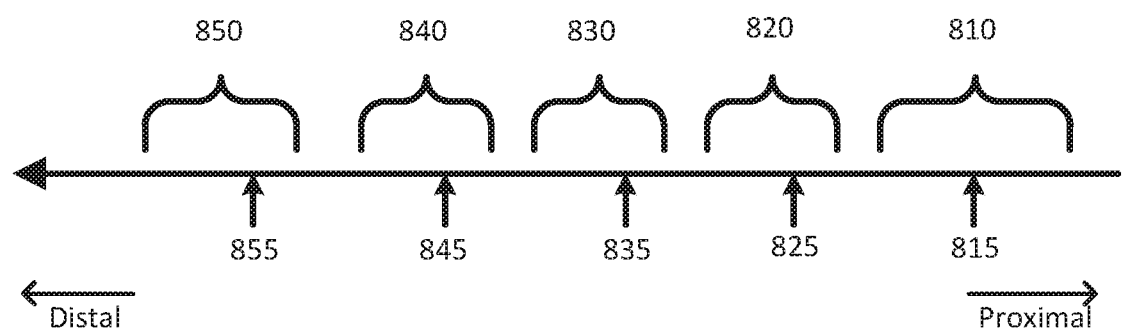
FIG. 8 is a simplified diagram of nominal position set point locations for an end effector according to some embodiments.

According to some embodiments, a model of expected end effector positions and ranges may be used to determine the expected end effector position from the end effector position determined during process 740. FIG. 8 is a simplified diagram of nominal position set point locations for an end effector according to some embodiments. As shown in FIG. 8, the DOF for the end effector is divided up into a number of non-overlapping ranges 810-850, with each range 810-850 corresponding to the nominal position of the end effector as triggered by the increase in actuation level detected by process 730. In some examples, region 810 may correspond to a range in the position of the DOF where non-presence of a staple cartridge may trigger the increase in actuation level, regions 820-840 may correspond to respective ranges in position of the DOF where a detent may trigger the increase in actuation level for different staple lengths, and/or range 850 may correspond to a range in the position of the DOF where a previously used staple cartridge may be detected. Each of the ranges 810-850 is further associated with a corresponding nominal position 815-855 that may represent most likely expected positions for the end effector within each of the corresponding ranges 810-850. In some examples, the locations, sizes, and nominal positions 815-855 for each of the ranges 810-850 may be determined empirically, such as by measuring variations among end effectors, staple cartridges, and/or instruments and using the distribution of measurements to determine the most likely ranges 810-850 and nominal positions 815-855.

Referring back to FIG. 7 and process 750, the expected position for the end effector is determined by comparing the position of the end effector determined during process 740 to each of the ranges 810-850. When the position of the end effector determined during process 740 falls within one of the ranges 810-850, the nominal position 815-855 for that range represents the expected position for the end effector. In some embodiments, when the position of the end effector determined during process 740 does not fall within any of the ranges 810-850, the control unit may select the nearest range, abort method 700, alert the operator, request clarification from the operator, and/or any combination thereof.

At a process 760, a corrective position offset is determined based on the position of the end effector detected during process 740 and the nominal position of the end effector determined during process 750. In some examples, the corrective position offset is determined by subtracting the position of the end effector from the nominal position of the end effector as this represents the amount that the position of the end effector determined during process 740 is most likely to be from its actual position as indicated by the location of the detent or other feature that resulted in the increased actuation level. In some examples, the corrective position offset may also be bounded by expected maximum deviations based on theoretical or empirical characterizations of the end effector.

At a process 770, a position set point is adjusted based on the corrective position offset determined during process 760. Further actuation of the end effector may include driving the end effector to one or more positions (such as a full distal position in order to fire all the staples in a staple cartridge and/or to complete a cutting operation). Each of these positions may correspond to a position set point which may be adjusted by adding the corrective position offset to the position set point to obtain an adjusted position offset, which more accurately reflects an actual amount the actuator has to actuate the drive mechanism to actually reach the desired position set point.

At a process 780, the end effector is actuated to the adjusted position set point determined during process 770. In some examples, the actuation of process 780 may be similar to the actuation used during process 710 except that the actuation occurs to the adjusted set point rather than based on an actuation level. In some examples, the adjusted position set point may be a set point for a position control loop in a control unit for the DOF. In some examples, the actuation to the adjusted set point may additionally be subject to a current, force, torque, and/or similar limit. Once the end effector is actuated to the adjusted position set point, additional position set points may be adjusted by returning to process 780.

Figure 9:
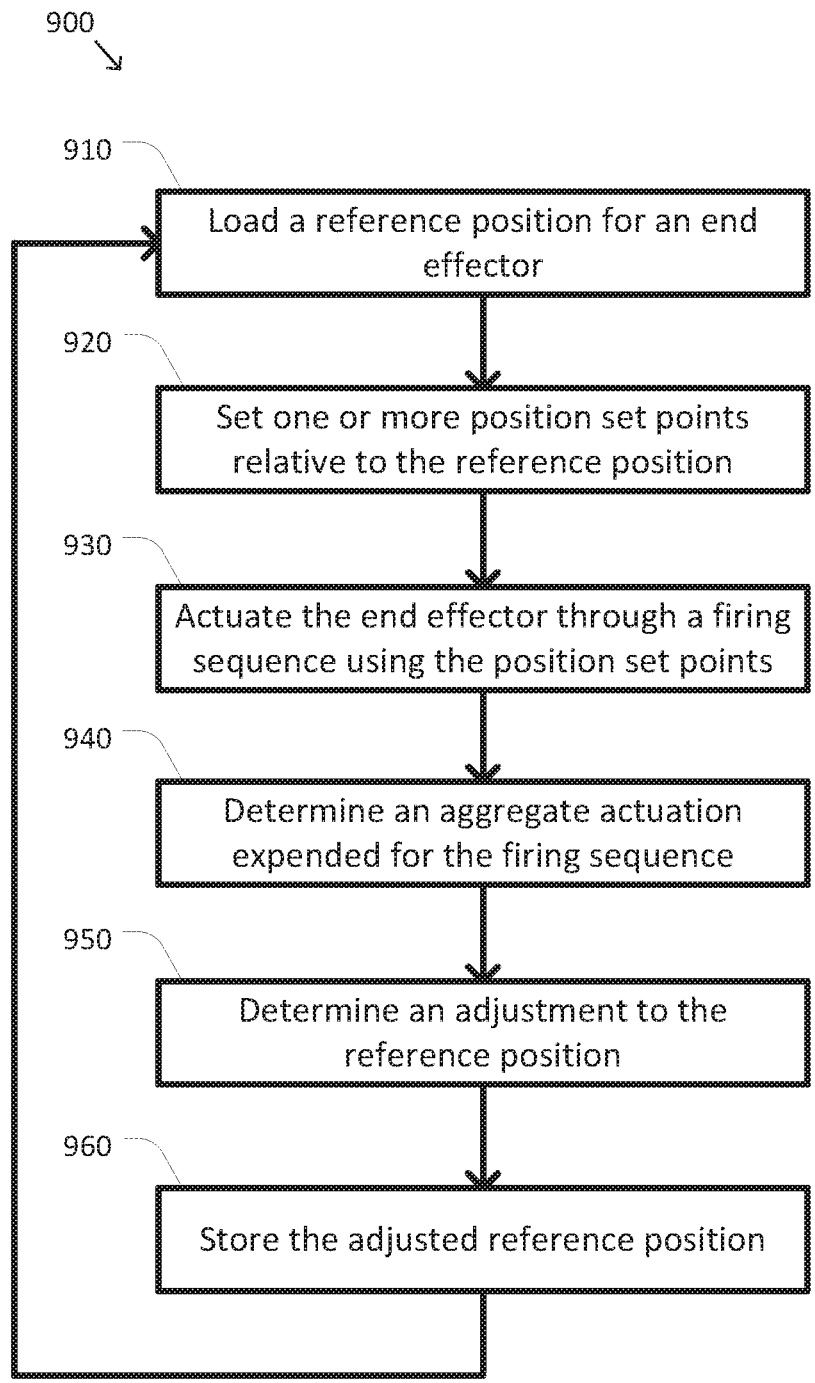
FIG. 9 is a simplified diagram of a method for correcting position set points of an end effector over repeated operations of an instrument according to some embodiments.

FIG. 9 is a simplified diagram of a method 900 for correcting position set points of an end effector over repeated operations of an instrument according to some embodiments. One or more of the processes 910-960 of method 900 may be implemented, at least in part, in the form of executable code stored on non-transitory, tangible, machine readable media. This executable code, when run by one or more processors (e.g., the processor 150 in control unit 140), may cause the one or more processors to perform one or more of the processes 910-960. In some embodiments, method 900 may be performed by an application, such as control application 170. In some embodiments, method 900 may be used to control the actuation of a reciprocating element, such as reciprocating element 350, by actuating the reciprocating element to one or more position set points relative to a reference position of the reciprocating element. In some embodiments, the order of processes of method 900 may occur in a different order than those implied by the flow chart of FIG. 9. In some examples, processes 920 and 930 may be performed iteratively and/or concurrently. In some examples, process 940 may be performed concurrently with process 930.

At a process 910, a reference position for the end effector is loaded. To account for variations between individual end effectors, each individual end effector is assigned its own reference position. The reference position may account for manufacturing variations, wear and/or stress on the end effector (e.g., due to plastic deformation), and/or the like. In some examples, the reference position may be considered a zero position of the end effector. In some examples, the reference position is stored in a memory in the end effector or instrument and/or may be determined using a table and/or database accessible by the control unit based on an identifier for the end effector or the instrument.

At a process 920, one or more position set points are set relative to the reference position. The one or more position set points correspond to one or more positions as part of a firing sequence to which the end effector is actuated in order perform the firing sequence. In some examples, the first position of method 600 may correspond to one of the one or more position set points. Each of the one or more position set points of the firing sequence are set relative to the reference position so that the expected positions of the one or more set points are adjusted for the particular end effector being controlled.

At a process 930, the end effector is actuated through the firing sequence using the one or more position set points set during process. In some examples, the end effector, such as end effector 220, may be actuated by sending one or more control signals to an actuator, such as actuator in drive system 240, 410, and/or 510. A drive mechanism, such as drive mechanism 250, 400, and/or 500, may then transfer the actuation of the actuator to a DOF in the end effector. In some examples, the DOF may correspond to the distal and/or proximal motion of a reciprocating element, such as reciprocating element 350. In some examples, each of the one or more position set points may be used in turn as a set point for a position control loop in a control unit for the DOF. In some examples, the actuation to the adjusted set point may additionally be subject to a current, force, torque, and/or similar limit.

At a process 940, an aggregate actuation expended for the firing sequence is determined. As the end effector is actuated through the firing sequence during process 930, the actuation level of the end effector is monitored. In some examples, the actuation level may be determined by measuring and/or computing an amount of current being drawn by the actuator in the drive system and detected using a current sensor, a force or torque being applied by the actuator and detected using a force or torque sensor, and/or other factors indicative of actuation level. In some examples, combination of two or more of current, force, torque, and/or the like may be used to determine the actuation level. In some examples, the aggregate actuation may be determined by integrating the actuation level over time as the firing sequence is performed. In some examples, the integration may be performed by initializing the aggregate actuation to zero and then adding aggregation levels obtained at fixed intervals to the aggregate actuation. In some examples, the aggregate actuation may then be optionally multiplied by the length of the fixed intervals. In some examples, variable length intervals may alternatively be used with each respective aggregation level being multiplied by a length of its respective interval. In some examples, other numerical integration techniques may be used including the trapezoidal method, Romberg integration, Simpson's Rules, and/or the like. In some examples, the amount of the aggregated actuation may vary based on a type of end effector, a type of the material being manipulated using the end effector, a procedure being performed, and/or the like. In some examples, the aggregate actuation may be in a range from 1000 to 8000 N·s when the actuation level is based on force over a period of time.

At a process 950, an adjustment to the reference position is determined. In some examples, the aggregate actuation determined during process 940 provides an approximation to the stress applied to the end effector and may be predictive of an amount of plastic deformation that occurs in the end effector and/or in a driving mechanism used to actuate the end effector. In some examples, the adjustment to the reference position may be determined by modeling the drive mechanism using a model according to Equation 2, where c is a spring modeling constant. In some examples, an adjusted reference is then determined by adding the adjustment to the reference position to the reference position loaded during process 910.

$$\Sigma(\text{actuation level}) \cdot c = \text{adjustment} \qquad \text{Equation 2}$$

In some examples, when the actuation level corresponds to applied force, c may be in a range from $3 \times 10^{-5}$ to $6 \times 10^{-5}$ mm/(N·s). In some examples, the modeling constant c may be set based on type of end effector or instrument. In some examples, the modeling constant c may be determined empirically for each end effector and/or instrument and stored in a memory in the end effector or instrument and/or may be determined using a table and/or database accessible by the control unit based on an identifier for the end effector or the instrument.

At a process 960, the adjusted reference position determined during process 960 is stored and replaces the reference position loaded during process 910. In some examples, the adjusted reference position is stored in the memory in the end effector or instrument and/or the table and/or database where it is associated with the identifier for the end effector or the instrument.

The end effector may then be actuated through additional firing sequences with the reference position being adjusted for teach of the additional firing sequences by repeating method 900.

As discussed above and further emphasized here, FIGS. 6, 7, and 9 are merely examples which should not unduly limit the scope of the claims. One of ordinary skill in the art would recognize many variations, alternatives, and modifications. In some embodiments, method 900 may be used in combination with method 600 and/or 700 with method 900 providing adjustments to the reference position for each firing sequence to account for plastic deformation and/or other wear and methods 600 and/or 700 being used for additional correction during the firing sequence to account for additional variations (e.g., in a staple cartridge) and/or elastic deformation during the firing sequence.

Some examples of control units, such as control unit 140 may include non-transitory, tangible, machine readable media that include executable code that when run by one or more processors (e.g., processor 150) may cause the one or more processors to perform the processes of methods 600, 700, and/or 900. Some common forms of machine readable media that may include the processes of methods 600, 700, and/or 900 are, for example, floppy disk, flexible disk, hard disk, magnetic tape, any other magnetic medium, CD-ROM, any other optical medium, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A system for actuating an instrument, the system comprising:
   an instrument comprising an end effector, and a drive mechanism for actuating the end effector; and
   a control unit configured to:
   actuate the end effector using the drive mechanism;
   determine an actuation level of an actuator during the actuation;

determine whether the actuation level is above a threshold actuation level; and
in response to determining that the actuation level is above the threshold-actuation level:
determine a position of the end effector;
identify a nominal position associated with the determined position of the end effector;
determine a position offset based on the nominal position and the determined position of the end effector;
adjust a position set point based on the position offset, the position set point corresponding to a desired position for the end effector; and
actuate the end effector to the adjusted position set point using the drive mechanism.

2. The system of claim 1, wherein the threshold actuation level is:
stored in the end effector or the instrument; or
retrieved from a table or database.

3. The system of claim 1, wherein the end effector is a stapling device.

4. The system of claim 1, wherein the actuation level of the actuator is a current level, a force level, or a torque level of the actuator for actuating the drive mechanism.

5. The system of claim 1, wherein the determined position of the end effector corresponds to:
a detent on the end effector;
or a detent on a stapling cartridge.

6. The system of claim 5, wherein the detent on the end effector or the stapling cartridge identifies a length of staples in the staple cartridge, the staple cartridge whose staples have been fired, or absence of the staple cartridge.

7. The system of claim 1, wherein to determine the nominal position the control unit is configured to:
determine which of a plurality of ranges the determined position of the end effector is in; and
select, as the nominal position, a nominal position for a first range of the plurality of ranges that the determined position of the end effector is in.

8. The system of claim 7, wherein:
one or more of the plurality of ranges corresponds to a length of staples in a staple cartridge; or
one of the plurality of ranges corresponds to an absence of a stapling cartridge in the end effector; or
one of the plurality of ranges corresponds to a stapling cartridge whose staples have previously been fired.

9. The system of claim 1, wherein the position offset is a difference between the nominal position and the determined position of the end effector.

10. The system of claim 1, wherein to adjust the position set point the control unit is configured to add the position offset to the position set point.

11. A method of actuating an end effector of an instrument using a control unit, the method comprising:
actuating the end effector using a drive mechanism;
determining an actuation level of an actuator during the actuation;
determining whether the actuation level is above a threshold actuation level; and
in response to determining that the actuation level is above the threshold actuation level:
determining a position of the end effector;
identifying a nominal position associated with the determined position of the end effector;
determining a position offset based on the nominal position and the determined position of the end effector;
adjusting a position set point based on the position offset, the position set point corresponding to a desired position for the end effector; and
actuating the end effector to the adjusted position set point using the drive mechanism.

12. The method of claim 11, wherein the actuation level of the actuator is a current level, a force level, or a torque level of the actuator for actuating the drive mechanism.

13. The method of claim 11, wherein:
the determined position of the end effector corresponds to a detent on the end effector or a detent on a stapling cartridge; and
the detent on the end effector or the stapling cartridge identifies:
a length of staples in the staple cartridge,
the staple cartridge whose staples have been fired, or
absence of the staple cartridge.

14. The method of claim 11, wherein determining the nominal position comprises:
determining which of a plurality of ranges the determined position of the end effector is in; and
selecting, as the nominal position, a nominal position for a first range of the plurality of ranges that the determined position of the end effector is in.

15. The method of claim 14, wherein:
one or more of the plurality of ranges corresponds to a length of staples in a staple cartridge; or
one of the plurality of ranges corresponds to an absence of a stapling cartridge in the end effector; or
one of the plurality of ranges corresponds to a stapling cartridge whose staples have previously been fired.

16. The method of claim 11, wherein:
the position offset is a difference between the nominal position and the determined position of the end effector; and
adjusting the position set point comprises adding the position offset to the position set point.

17. One or more non-transitory computer-readable media having stored thereon a plurality of machine-readable instructions that, when executed by one or more processors associated with a computer-assisted device, are adapted to cause the one or more processors to perform a method comprising:
actuating an end effector using a drive mechanism;
determining an actuation level of an actuator during the actuation;
determining whether the actuation level is above a threshold actuation level; and
in response to determining that the actuation level is above the threshold actuation level:
determining a position of the end effector;
identifying a nominal position associated with the determined position of the end effector;
determining a position offset based on the nominal position and the determined position of the end effector;
adjusting a position set point based on the position offset, the position set point corresponding to a desired position for the end effector; and
actuating the end effector to the adjusted position set point using the drive mechanism.

18. The one or more non-transitory computer-readable media of claim 17, wherein determining the nominal position comprises:
determining which of a plurality of ranges the determined position of the end effector is in; and selecting, as the nominal position, a nominal position for a first range of the plurality of ranges that the determined position of the end effector is in.

19. The one or more non-transitory computer-readable media of claim 18, wherein:
   one or more of the plurality of ranges corresponds to a length of staples in a staple cartridge; or
   one of the plurality of ranges corresponds to an absence of a stapling cartridge in the end effector; or
   one of the plurality of ranges corresponds to a stapling cartridge whose staples have previously been fired.

20. The one or more non-transitory computer-readable media of claim 17, wherein:
   the position offset is a difference between the nominal position and the determined position of the end effector; and
   adjusting the position set point comprises adding the position offset to the position set point.

* * * * *